United States Patent
Kuljis et al.

(10) Patent No.: US 7,218,101 B2
(45) Date of Patent: May 15, 2007

(54) EDDY CURRENT METHOD OF INSPECTING A PRESSURE VESSEL SHELL

(75) Inventors: Zoran R. Kuljis, Granby, CT (US); Richard J. Vannucci, East Longmeadow, MA (US)

(73) Assignee: Westinghouse Electric Co. LLC, Pittsburgh, PA (US)

( * ) Notice: Subject to any disclaimer, the term of this patent is extended or adjusted under 35 U.S.C. 154(b) by 75 days.

(21) Appl. No.: 11/007,514

(22) Filed: Dec. 8, 2004

(65) Prior Publication Data

US 2006/0055401 A1    Mar. 16, 2006

Related U.S. Application Data

(60) Provisional application No. 60/531,390, filed on Dec. 19, 2003.

(51) Int. Cl.
*G01N 27/82* (2006.01)
*G01N 27/72* (2006.01)
*G21C 17/00* (2006.01)

(52) U.S. Cl. .................... 324/219; 324/220; 324/238; 324/262; 376/249

(58) Field of Classification Search ........ 324/219–220, 324/228–243, 262; 376/249
See application file for complete search history.

(56) References Cited

U.S. PATENT DOCUMENTS

| | | | | |
|---|---|---|---|---|
| 4,797,613 | A | * | 1/1989 | Wentzell ..................... 324/220 |
| 4,855,677 | A | | 8/1989 | Clark, Jr. et al. |
| 5,256,966 | A | * | 10/1993 | Edwards ..................... 324/220 |
| 5,315,234 | A | * | 5/1994 | Sutton et al. ............... 324/242 |
| 5,327,080 | A | * | 7/1994 | Haller ......................... 324/219 |
| 5,396,800 | A | * | 3/1995 | Drinon et al. ................ 73/623 |
| 5,903,147 | A | * | 5/1999 | Granger et al. ............. 324/219 |
| 5,969,275 | A | | 10/1999 | Moe |
| 6,281,678 | B1 | * | 8/2001 | Auville ....................... 324/220 |
| 6,734,668 | B2 | | 5/2004 | Hils et al. |

* cited by examiner

*Primary Examiner*—Jay M. Patidar

(57) ABSTRACT

A pressure vessel penetration sidewall adjacent a tube installed in the penetration by a clearance fit is inspected by passing an eddy current probe having a pair of circumferential coils through the tube. Eddy currents are induced in the pressure vessel as the probe passes through the penetration tube and degradation of the pressure vessel adjacent the clearance is determined based upon the eddy currents induced in the pressure vessel by the probe.

15 Claims, 2 Drawing Sheets

EDDY CURRENT METHOD OF INSPECTING A PRESSURE VESSEL SHELL

CROSS REFERENCE

This application is a continuation of Provisional Patent Application No. 60/531,390 filed Dec. 19, 2003.

BACKGROUND OF THE INVENTION

The invention relates to a method of inspecting pressure vessels for corrosion wastage and other forms of degradation and more particularly to a method of inspecting the regions of pressure vessels adjacent penetration tubes installed with clearance fits and welded to the pressure vessels.

The penetration tubes welded to pressure vessels may become susceptible to stress corrosion cracking after years of on-line operation at high temperatures and high pressures. Micro-cracks may form and grow into leak paths through which the contained fluids may seep and eventually corrode the pressure vessels. Thus, it has been found that the penetration tubes extending through the heads of reactor pressure vessels in the primary systems of pressurized water nuclear reactors are susceptible to cracking. In one case, it was found that a crack had grown in a penetration tube beyond its J-groove weld and that primary water (which is a dilute boric acid solution) had leaked through the crack and corroded the shell of the pressure vessel so that a stainless steel liner was the only structure maintaining the pressure of the system. The nuclear industry now inspects the wetted surfaces of the heads of certain reactor pressure vessels in the course of each refueling outage in accordance with NRC Order EA-03-009. Thus, the wetted surfaces of the heads are inspected visually and the portions of the penetration tubes from the J-groove welds to two inches above the J-groove welds are inspected using ultrasonic, eddy current or dye penetrant techniques.

The Applicants have realized that the inspections now conducted by the nuclear industry may not detect chemical wastage or other degradation in the regions of pressure vessel penetrations adjacent clearances behind some penetration tubes (such as vents in the their heads) until boric acid residues from evaporated leaking water are visually detected on the outer surfaces of the heads during refueling outages.

SUMMARY OF THE INVENTION

It is an object of the present invention to provide a method of inspecting the penetrations of pressure vessels surrounding penetration tubes installed with clearance fits and welded to the pressure vessels. It is a further object to provide a method of inspecting such penetrations for degradation.

With these objects in view, the present invention resides in a method of inspecting a pressure vessel having an inner surface and an outer surface with a penetration extending therebetween. An eddy current probe is passed through a penetration tube installed in the penetration with a clearance fit and welded at the inner surface of the pressure vessel. Eddy currents are induced in the pressure vessel as the probe passes through the penetration tube and degradation of the pressure vessel adjacent the penetration tube is determined based upon the eddy currents induced in the pressure vessel by the probe. In preferred practices, the probe introduces eddy currents into the pressure vessel while it passes from either the inner or outer surface of the pressure vessel.

BRIEF DESCRIPTION OF THE DRAWINGS

The invention as set forth in the claims will become more apparent from the following detailed description of preferred practices hereof shown, by way of example only, in the accompanying drawings, wherein:

DESCRIPTION OF A PREFERRED PRACTICE

Figure 1:
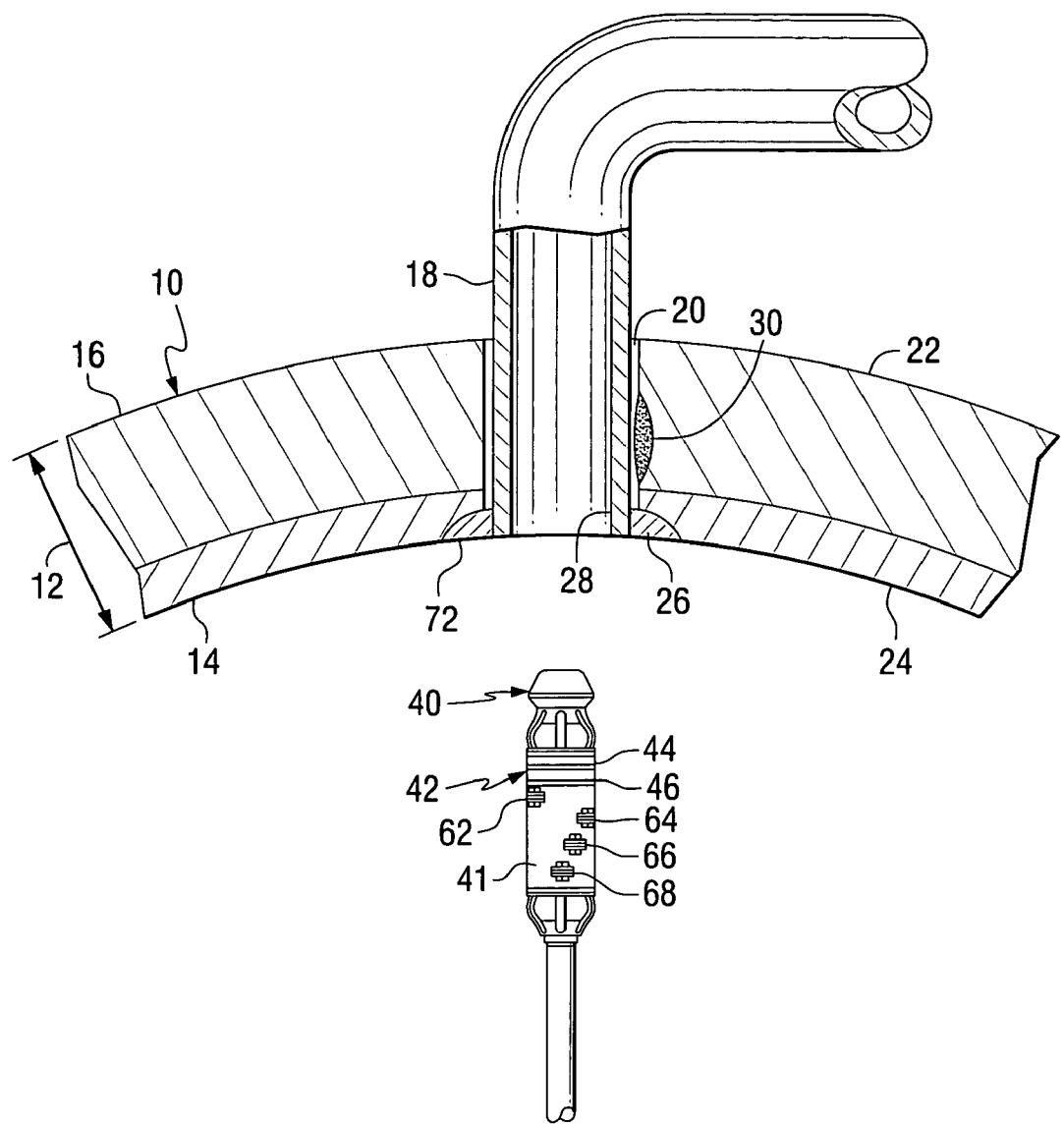
FIG. 1 is a fragmentary partially sectional view of a vent tube in a pressure vessel aligned with an eddy current probe for inspecting the pressure vessel and the vent tube.

The preferred practice of the present invention was made to inspect the regions of reactor pressure vessels adjacent their vent tubes for corrosion wastage or other degradation. Thus, FIG. 1 shows a reactor pressure vessel 10 having a thickness 12 defined by an inner surface 14 and an outer surface 16 with a penetration tube 18 extending through a penetration 20. Such reactor pressure vessels 10 may have a shell 22 of carbon or low alloy steel or other suitable structural material and an inner liner 24 of stainless steel or other suitable structural material. The penetration tube 18 is shown as a vent tube, which may be sometimes referred to as a vent pipe or simply as a vent. Vent tubes in reactor pressure vessels may be Schedule 160 one inch diameter pipes made of stainless steel, Alloy 600 or other suitable structural material. Such penetration tubes 18 may be installed with clearance fits on the order of one to three thousandths of an inch and then welded to the inner surfaces 14 of the pressure vessels 10. The welds 26 may be J-groove welds where the penetration tubes 18 extend from reactor pressure vessel heads. As shown, there is corrosion wastage 30 in a region adjacent the penetration tube 18, which may not physically contact the outer surface of the penetration tube 18. It should be noted that the relative size of the clearance and the wastage 30 region is shown out of proportion in FIG. 1 for purposes of illustration.

In the practice of the present invention, an eddy current probe 40 is passed through the penetration tube 18. Preferably, the probe 40 has a circumferential surface 41 and at least one circumferential coil. FIG. 1 shows a coil pair 42, including coils 44 and 46. The coil pair 42 induces eddy currents in the pressure vessel 10 as the probe 40 passes through the penetration tube 18. The two coils 44 and 46 may be electrically connected to oppose each other and operated in differential mode. The coils 44 and 46 may also operate in absolute mode. The two coils 44 and 46 may be operated at frequencies of between about 2 and about 100 kHz. For example, they may operate at 2, 4, 50 or 100 kHz. Probes 40 having a pair of circumferential coils 44 and 46 (sometimes known as "bobbin" coils) are commercially available from Zetec, Inc. of Issaquah, Wash. and other suppliers.

Degradation of the pressure vessel 10 adjacent the penetration tube 18, such as for example wastage 30 of sidewall 28, is determined based upon the eddy currents induced in the pressure vessel 10 by the coil pair 42. Tests conducted at 2 kHz and at 4 Hz using an Alloy 600 tube inserted within carbon steel rings having inner diameters of 0.01 inch and 0.1 inch greater than the tube diameter (to simulate gaps of 0.005 inch and 0.05 inch, respectively, in a pressure vessel), showed that eddy current signal responses in the impedance plane can detect differences in the clearance gaps between pressure vessels and penetration tubes.

In some practices of the present invention, the pressure vessel 10 may be inspected by introducing eddy currents into the pressure vessel 10 while the probe 40 passes from one surface 22 or 24 of the pressure vessel 10 to the other surface 22 or 24 of the pressure vessel 10. In a preferred practice, the entire thickness 12 of the pressure vessel 10 may be inspected in a single pass of the probe 40 through the penetration tube 18.

In some practices of the present invention, the penetration tube 18 itself may be inspected by a probe 40 also having multiple eddy current arrays (which are shown as four arrays 62–68 by FIG. 1) while the pressure vessel 10 is being inspected for degradation. Each array 62–68 may have several eddy current coils (for example, four coils spaced at 90°) around the circumference of the probe 40, which may be circumferentially offset from the coils of the other arrays. Preferably, there are at least twelve circumferentially spaced coils in the arrays when the inner diameters of the penetration tubes 18 do not exceed 0.614" inch. For inner diameters ranging from 0.614 to 0.815 inch, the array may consist of sixteen circumferentialy spaced coils. The eddy current coils in the arrays preferably are cross-point or, or plus point, coils and do not contact the inner surface of the penetration tube 18. A cross-point coil is in fact a differential pair of coils. In one practice, the primary examination frequency for such coils may be 400 kHz (differential mode only) and the secondary examination frequency may be 250 kHz. Such eddy current coils are commercially available under the designation "+Point" from Zetec, Inc. Preferably, the probe 40 is rotatable and the entire surface of the vent tube 18 from a height about six inches above outer surface 22 of the pressure vessel 10 to the bottom surface of the pressure vessel 10 can be inspected in a single vertical pass of the probe 40 while the pressure vessel is inspected for corrosion wastage or other indications of degradation.

Figure 2:
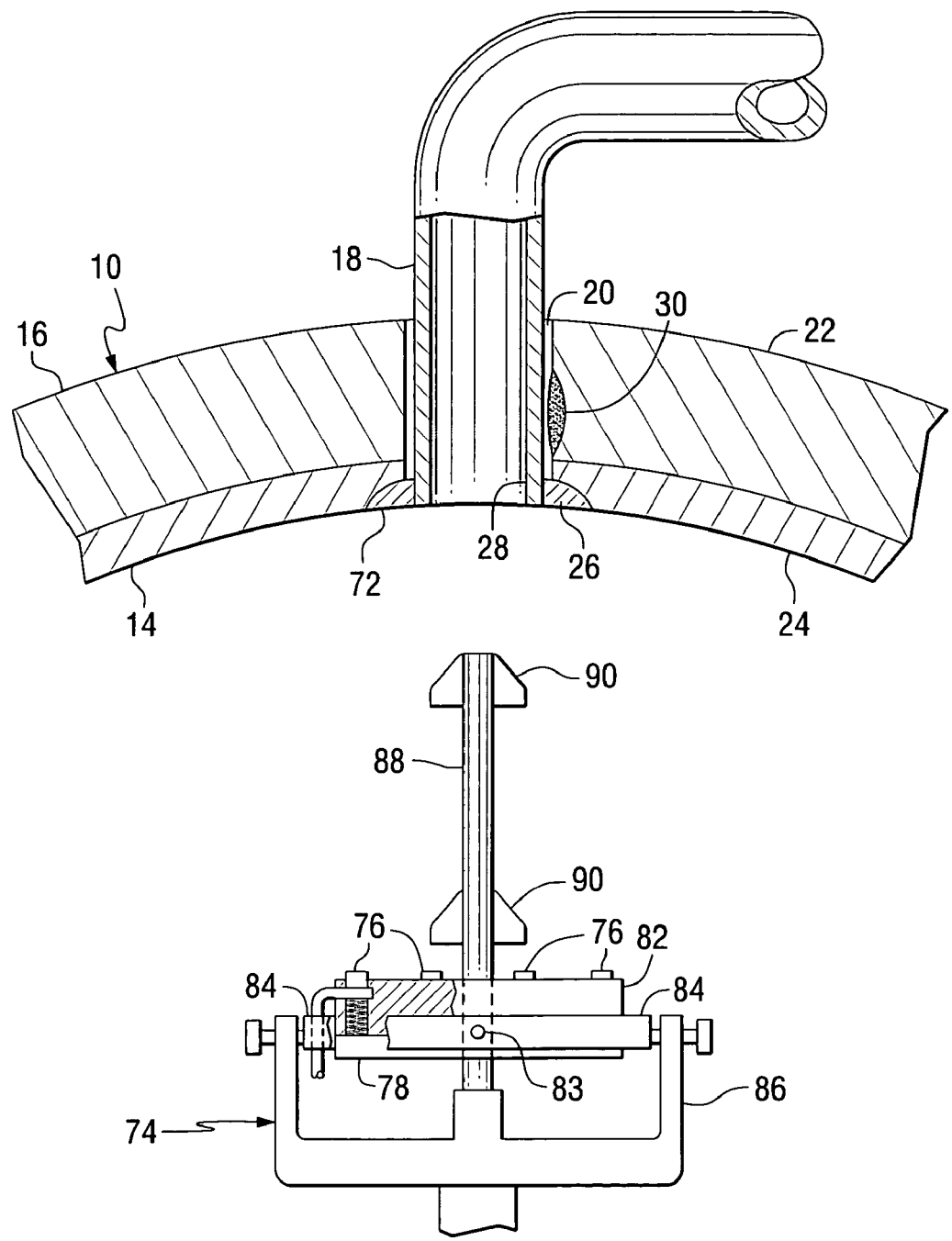
FIG. 2 is fragmentary partially sectional view of the vent tube of FIG. 1 aligned with a an eddy current probe for inspecting a vent tube weld.

In some practices of the present invention (for example, where all wetted surfaces of a reactor vessel head are inspected), either before or after the region of the pressure vessel 10 adjacent the penetration tube 18 is inspected for degradation, the weld 26 may be inspected with an array of eddy current coils. FIG. 2 shows a rotatable tool 74 having an array of eddy current coils (represented by four coils 76) for inspecting the weld 26. In preferred practices, the weld 26 may be inspected by one rotation of the array of coils 76.

The tool 74 shown in FIG. 2 preferably has up to thirty-two radially and circumferentially offset eddy current coils 76 or more to provide full coverage of the weld surface 72. As shown, the coils 76 may be urged by springs (represented by spring 78) against a plate 82. The coils 76 may have wear resistant caps or plastic surface riding shoes to extend their lives. The coils 76 may be cross point, or plus point, eddy current coils, such as +Point coils commercially available from Zetec, Inc., operated in differential mode. In some practices, the frequencies may be 250 (primary) and 600 (secondary) kHz in differential mode. The preferred operating range is 50–600 kHz and more preferably 100–600 kHz.

As is shown in FIG. 2, the plate 82 may be supported on gimble screws (shown by screw 83) extending from a gimble ring 84 and yoke 86 arrangement so that the plate 82 may be oriented at any angle and the eddy current coils 76 may be maintained in constant contact with the surface 72 of the weld 26. As shown, the tool 74 may have a pivotally connected centering shaft 88 extending through the middle of the plate 82 with guides 90 that may be inserted into the penetration tube 18 to center the tool 74. The tool 74 may be manually positioned against the weld 26 (e.g., at the end of a hand held shaft) or positioned remotely using a robotic device. In a preferred practice, the weld 26 may inspected by one rotation of the array of eddy current coils 76.

While a present preferred embodiment of the present invention has been shown and described, it is to be understood that the invention may be otherwise variously embodied within the scope of the following claims of invention.

What is claimed is:

1. A method of inspecting a pressure vessel having a shell extending between an inner surface and an outer surface and a penetration extending through the shell from the inner surface to the outer surface, comprising the steps of:
    passing an eddy current probe through a penetration tube installed in the penetration with a clearance fit and welded at the inner surface of the pressure vessel;
    inducing eddy currents in the pressure vessel as the probe passes through the penetration tube; and
    determining the degradation of the pressure vessel shell in the region adjacent the penetration tube based upon eddy currents induced in the pressure vessel by the probe.

2. The method of claim 1, wherein the probe introduces eddy currents into the pressure vessel while it passes from either the inner or outer surface of the pressure vessel to the other surface of the pressure vessel.

3. The method of claim 2, wherein the pressure vessel is inspected in one pass of the probe through the penetration.

4. The method of claim 1, wherein the eddy currents are induced in the pressure vessel by at least one circumferential coil.

5. The method of claim 4, wherein the eddy currents are induced in the pressure vessel by a pair of circumferential coils.

6. The method of claim 1, wherein the probe also has a multiple array of eddy current coils, comprising the step of:
    inspecting the penetration tube with the multiple array of eddy current coils.

7. The method of claim 6, wherein the pressure vessel and the penetration tube are inspected in one pass of the probe through the penetration.

8. The method of claim 1, including the step of:
    inspecting the weld with an array of eddy current coils.

9. The method of claim 8, wherein the array of eddy current coils is rotated to inspect the weld.

10. The method of claim 9, wherein the weld is inspected in one 360° rotation of the array of eddy current coils.

11. The method of claim 10, wherein the pressure vessel and the penetration tube are inspected by one pass of the probe through the penetration from either the inner or outer surface of the pressure vessel to the other surface of the pressure vessel.

12. The method of claim 1, wherein the step of determining the degradation of the pressure vessel shell comprises determining the degradation across a gap of between 5 and 50 thousandths of an inch.

13. The method of claim 12, wherein the step of determining the degradation of the pressure vessel shell comprises determining the degradation across a gap of about 50 thousandths of an inch.

14. A method of inspecting a pressure vessel having an inner surface and an outer surface and a penetration extending therebetween, comprising the steps of:
    passing a first eddy current probe through a penetration tube installed in the penetration with a clearance fit and welded at the inner surface of the pressure vessel; and inspecting the entire thickness between the inner surface and the outer surface of the pressure vessel and the penetration tube in one pass of the first eddy current probe between the inner surface and the outer surface of the pressure vessel.

15. The method of claim 14, comprising the additional step of:
inspecting the weld in one 360° rotation of a second eddy current probe.

* * * * *